US00PP17764P3

(12) United States Plant Patent
Olesen

(10) Patent No.: US PP17,764 P3
(45) Date of Patent: May 29, 2007

(54) SHRUB ROSE PLANT NAMED 'POULTC007'

(50) Latin Name: *Rosa hybrida*
Varietal Denomination: Poultc007

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 275 days.

(21) Appl. No.: 11/131,738

(22) Filed: May 17, 2005

(65) Prior Publication Data

US 2006/0265790 P1 Nov. 23, 2006

(51) Int. Cl.
*A01H 5/00* (2006.01)

(52) U.S. Cl. ..... Plt./104

(58) Field of Classification Search ..... Plt./104, Plt./145

See application file for complete search history.

*Primary Examiner*—Kent Bell
*Assistant Examiner*—June Hwu

(57) ABSTRACT

A new garden rose plant of the shrub class which has abundant, yellow flowers and attractive, dark green, glossy foliage. This new and distinct variety has shown to be uniform and stable in the resulting generations from asexual propagation.

1 Drawing Sheet

Botanical classification: *Rosa hybrida.*
Variety denomination: 'Poultc007'.

SUMMARY OF THE INVENTION

The present invention constitutes a new and distinct variety of garden rose plant which originated from a controlled crossing between the female seed parent plant, an unnamed seedling, and the male pollen parent plant, an unnamed seedling. The two parents were crossed during the summer of 1997, and the resulting seeds were planted in a controlled environment in Fredensborg, Denmark. The new variety is named 'Poultc007'.

The new variety may be distinguished from the female parent, by the following combination of characteristics:

1. 'Poultc007' has a low growth height of 40 to 60 cm while the female parent plant has a medium growth height of 60 to 100 cm.
2. 'Poultc007' exhibits flowers with a smaller diameter than those of the unnamed female parent.
3. 'Poulc007' develops flower buds in greater quantity per flowering stem than the female parent plant.

The new variety may be distinguished from its pollen parent by the following combination of characteristics:

1. The pollen parent has a light yellow flower color, while 'Poultc007' has medium yellow flower color.
2. Open flowers of the pollen parent are 32 mm in diameter while flowers of 'Poultc007' are 60 mm in diameter.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots;
3. Disease resistance;
4. Dark green attractive foliage;
5. Suitability for growth in a container.

This combination of qualities is not present in previously available commercial cultivars of this type, known to the inventors, and distinguish 'Poultc007' from all other varieties of which we are aware.

As part of the rose development program, Mogens N. Olesen germinated the seeds from the aforementioned hybridization during winter of 1997 and conducted evaluations on the resulting seedlings in a controlled environment in Fredensborg, Denmark.

'Poultc007' was selected in the spring 1998 by the inventor as a single plant from the progeny of the aforementioned hybridization.

Asexual reproduction of 'Poultc007' by traditional budding and rooted cuttings was first done by Mogens N. Olesen in his nursery in Fredensborg, Denmark in July, 1998. This initial and other subsequent asexual propagations conducted in controlled environments have demonstrated that the characteristics of 'Poultc007' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poultc007'.

Specifically illustrated in the drawing

FIG. 1.1; Flower petals, detached, and open flower;

FIG. 1.2; Sepals, pedicel, receptacle, and reproductive flower parts;

FIG. 1.3; Cluster of flower buds showing attachment to peduncle;

FIG. 1.4; Mature and juvenile leaf showing anthocyanin;

FIG. 1.5; Juvenile leaves attached to stem showing anthocyanin;

FIG. 1.6; Bare stem exhibiting thorns;

DETAILED DESCRIPTION OF THE VARIETY

The following is a description of 'Poultc007', as observed in its growth in a field nursery in Jackson County, Oreg. Observed plants are 2 years of age, grown on *Rosa multiflora* understock. Color references are made using The Royal Horticultural Society (London, England) Color Chart published in 2001, except where common terms of color are used.

For a comparison, several physical characteristics of the rose variety 'Poulgode', a rose variety from the same inventors described and illustrated in U.S. Plant patent application Ser. No. 11/042,257 dated Jan. 24, 2005, which is a continuation of 10/782,360 dated Feb. 18, 2004 (now abandoned), which is a continuation of 09/259,884 dated Feb. 27, 1999 (now abandoned), are compared to 'Poultc007' in Chart 1.

CHART 1

| | 'Poultc007' | Poulgode' |
|---|---|---|
| Bud color when sepals first divide | Orange Group 24C to 24B blend. | Yellow Group 12C. |
| Flower bloom number of normal petals | 22. | 35 to 45. |
| Average flower diameter when open | 60 mm. | 35 to 45 mm. |

FLOWER AND FLOWER BUD

Blooming habit: Continuous.

Flower bud:

*Size.*—Upon opening, 25 mm in length from base of receptacle to end of bud. Diameter is 13 mm.

*Bud form.*—Broad based, pointed ovoid.

*Bud color.*—As sepals unfold, petals are Orange Group 24B to 24C blend. At ¼ opening petals are Orange Group 24B with margins Yellow-Orange Group 18A. Sepal Upper Surface: Color: Yellow-Green Group 144B. Surface: Weak to medium pubescence observed. Sepal Lower Surface: Color: Yellow-Green Group 144A. Light anthocyanic pigments Greyed-Red Group 178A observed. Texture: Smooth. Sepal Shape: Sepal apex is cirrhose. Base is flat at union with receptacle. Sepal Margin: Margins have weak foliaceous appendages on three of the five sepals and few stipitate glands. Size: Normally 25 m (l)×7 mm (w).

*Receptacle.*—Surface: Smooth. Shape: Urn shaped. Size: On average 7 mm (h)×7 mm (w). Color: Yellow-Green Group 144A. Anthocyanic pigments the color of Greyed-Orange Group 172A observed.

*Pedicel.*—Surface: Slightly rough with small prickles. Length: 30 mm average length. Diameter: 3 mm on average. Color: Yellow-Green Group 144A. Anthocyanic pigments Greyed-Orange Group 172B observed. Strength: Medium.

*Borne.*—In clusters or cymes with 3 to 7 flower buds per flowering stem.

Flower bloom:

*Fragrance.*—None.

*Duration.*—The blooms have a duration on the plant of approximately 7 to 10 days. Afterwards, petals fall cleanly away from plant.

*Size.*—Flower diameter is 60 mm on average when open. Depth is normally 28 mm.

*Form.*—Semi-double flowers open fully, almost flat, to expose reproductive flower parts.

Petal count: 22 petals under normal conditions 8 of which are petaloids.

Flower color:

*Upon opening, petals.*—Upper Surface: Marginal and middle zones are a blend of Yellow Group 13B to Yellow-Orange Group 14C. Lower Surface: Orange Group 26B with narrow margins of Yellow 13C.

*Upon opening, basal petal spots.*—Upper Surface: Yellow Group 13A. Lower Surface: None.

*After opening, petals.*—Upper Surface: At basal zone, Yellow-Orange Group 14B. Middle and marginal zones are Yellow Group 13B to 13C blended. Lower Surface: Orange Group 26B. Margins are Yellow Group 13C.

*After opening, basal petal spots.*—Upper Surface: None. Lower Surface: Yellow Group 13B.

General tonality: No change in tonality at the end of the $7^{th}$ day. Afterwards, general tonality is Yellow-Orange Group 18A to 18B.

Petals:

*Petal reflex.*—Flat.

*Margin.*—Entire and uniform with weak undulations of margin observed.

*Shape.*—Generally broad elliptical to rounded. Apex: Rounded. Base: Rounded, occasionally acute.

*Size.*—On average, 31 mm (l)×32 mm (w).

*Texture.*—Smooth.

*Thickness.*—Average.

*Arrangement.*—Not Formal.

Petaloids:

*Quantity.*—Normally 8.

*Color.*—Upper Surface: At basal zone, Yellow-Orange Group 14B. Middle and marginal zones are Yellow Group 13B to 13C blended. Lower Surface: Orange Group 26B. Margins are Yellow Group 13C.

*Size.*—15 mm (l)×8 mm (w).

*Shape.*—Irregular.

Reproductive organs:

*Pistils.*—Length: 5 mm. Quantity: 100 on average.

*Pollen.*—None observed.

*Anthers.*—Size: 3 mm in length. Color: Yellow Group 12B/C. Quantity: 130 average.

*Filaments.*—Color: Yellow-Orange Group 17A. Length: 6 mm. Quantity: 130.

*Stigmas.*—Superior in location to the length of the filaments and the height of the anthers. Color: Yellow Group 11A.

*Styles.*—Color: Red Group 53C. Yellow-Green Group 145D at base.

*Hips.*—None observed in the field nursery in Jackson County Oreg.

PLANT

Plant growth: Upright to bushy. When grown as a budded field grown plant on *Rosa multiflora* understock, the average height of the plant is 40 to 60 cm. Normal spread is 60 cm.

Stems:

*Color.*—Young wood: Yellow-Green Group 144B. Anthocyanic intonations the color of Greyed-Red 181A observed. Older wood: Yellow-Green Group 144B to Yellow-Green Group 145A.

*Length.*—On average, canes are 40 to 50 cm from the base of the plant to the flowering portion.

*Diameter.*—Normally 8 mm.

*Internodes.*—40 mm average distance between nodes.

*Surface texture.*—Young wood: Smooth. Older wood: Smooth.

Thorns:

*Incidence.*—Generally 7 thorns per 10 cm of stem.

*Color.*—Juvenile thorns: Greyed-Orange Group 172B.

*Shape.*—Upper side: Concave. Lower side: Concave.

Plant foliage: Normal number of leaflets on normal leaves in middle of the stem: 5 to 7 leaflets.

*Compound leaf size.*—110 mm (l)×85 mm (w).

*Quantity.*—5 leaves per 10 cm of stem on average.

*Color.*—Mature Foliage: Upper surface: Yellow-Green Group 147A. Lower surface: Yellow-Green Group 146B. Juvenile Foliage: Upper surface: Green Group 146A. Lower surface: Green Group 146B.

Plant leaves and leaflets:

*Stipules.*—Size: 15 mm in length. Margins: Finely serrated with stipitate glands. Color: Yellow-Green Group 144A.

*Petiole.*—Length: Normally 30 mm. Diameter: 2 mm. Upper surface: Color: Yellow-Green Group 146A with light intonations of Greyed-Orange Group 174B. Lower surface: Color: Yellow-Green Group 144B. Observations: Stipitate glands and thorns observed.

*Rachis.*—Length: 45 mm. Above: Color: Yellow-Green Group 146A with light intonations of Greyed-Orange Group 174B to Greyed-Purple Group 184B. Underneath: Color: Yellow-Green Group 144B. Observations: Stipitate glands and numerous thorns and prickles observed.

*Leaflet.*—Size: Normally 45 mm (l)×32 mm (w). Edge: Serrated. Shape: Generally ovate. Base: Rounded. Apex: Cuspidate. Texture: Smooth. Thickness: Average. Arrangement: Odd pinnate. Venation: Reticulate. Glossiness: Glossy.

Disease resistance: Above average resistance to powdery and downy mildew, rust, black spot, and *Botrytis* under normal growing conditions in Jackson County, Oreg.

Cold hardiness: The variety 'Poultc007' has been found to be cold tolerant to USDA Cold Hardiness Zone 6.

It is claimed:

1. A new and distinct variety of rose plant of the shrub rose class named 'Poultc007', illustrated and described herein, due to its abundant yellow flowers, dark green glossy foliage, disease resistance, and extended period of bloom.

* * * * *

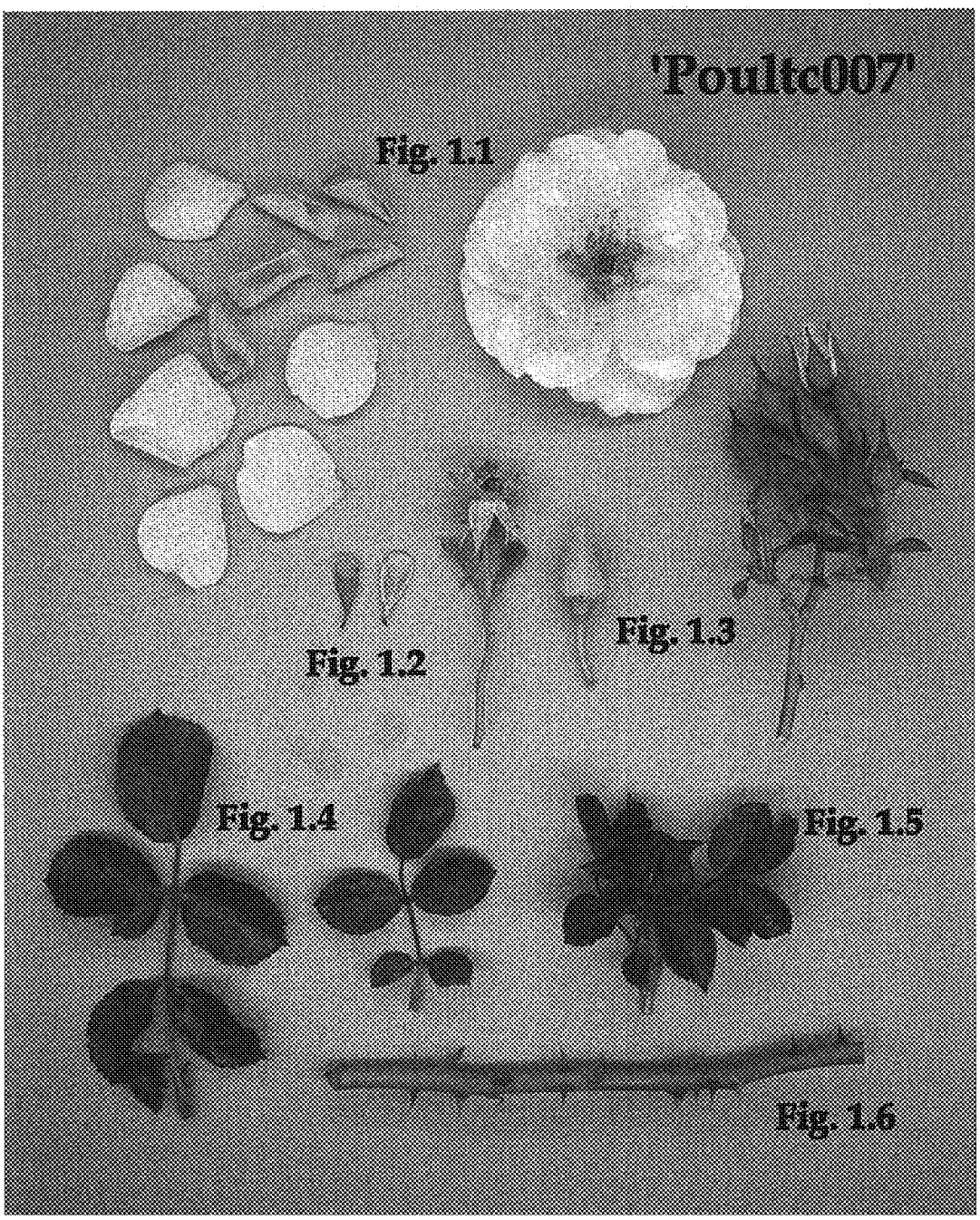
'Poultc007'
Fig. 1.1
Fig. 1.2
Fig. 1.3
Fig. 1.4
Fig. 1.5
Fig. 1.6